(12) United States Patent
Siegl et al.

(10) Patent No.: US 11,028,248 B2
(45) Date of Patent: Jun. 8, 2021

(54) SYSTEM AND PROCESS FOR RECYCLING CONTAMINATED POLYOLEFINS

(71) Applicant: ALPLA WERKE ALWIN LEHNER GMBH & CO. KG, Hard (AT)

(72) Inventors: Robert Siegl, Dornbirn (AT); Andreas Weber, Thuringen (AT)

(73) Assignee: ALPLA WERKE ALWIN LEHNER GMBH & CO. KG

( * ) Notice: Subject to any disclaimer, the term of this patent is extended or adjusted under 35 U.S.C. 154(b) by 84 days.

(21) Appl. No.: 16/462,170

(22) PCT Filed: Nov. 9, 2017

(86) PCT No.: PCT/EP2017/078813
§ 371 (c)(1),
(2) Date: May 17, 2019

(87) PCT Pub. No.: WO2018/091356
PCT Pub. Date: May 24, 2018

(65) Prior Publication Data
US 2019/0330439 A1 Oct. 31, 2019

(30) Foreign Application Priority Data
Nov. 17, 2016 (CH) ........................ 1523/16

(51) Int. Cl.
| | | |
|---|---|---|
| *C08J 11/08* | (2006.01) | |
| *B29B 17/02* | (2006.01) | |
| *B29K 105/26* | (2006.01) | |
| *A61L 11/00* | (2006.01) | |
| *A61L 2/00* | (2006.01) | |

(52) U.S. Cl.
CPC ............... *C08J 11/08* (2013.01); *B29B 17/02* (2013.01); *A61L 2/00* (2013.01); *A61L 11/00* (2013.01); *B29B 2017/0293* (2013.01); *B29K 2105/26* (2013.01); *C08J 2323/06* (2013.01); *C08J 2323/12* (2013.01)

(58) Field of Classification Search
CPC ... A61L 2/00; A61L 2/18; A61L 11/00; A61L 2202/00; A61L 2202/23; C08L 2207/20; A62D 2101/20
USPC ................................. 521/47; 134/23
See application file for complete search history.

(56) References Cited

U.S. PATENT DOCUMENTS

| | | | | |
|---|---|---|---|---|
| 3,781,253 A * | 12/1973 | Kashiwa et al. | ...... | C08F 4/6548 526/124.2 |
| 5,368,796 A | 11/1994 | Lorenz et al. | | |
| 6,133,329 A * | 10/2000 | Shieh | ................. | C08G 18/4018 521/131 |
| 6,545,061 B1 * | 4/2003 | Murdoch | ............. | C08G 63/183 521/48 |
| 2002/0128394 A1 | 9/2002 | Gorski et al. | | |

FOREIGN PATENT DOCUMENTS

| | | |
|---|---|---|
| DE | 4207370 A1 | 9/1993 |
| DE | 4233740 A1 | 4/1994 |
| DE | 102004002159 A1 | 8/2005 |
| WO | 03106546 A1 | 12/2003 |
| WO | 2018091356 A1 | 5/2018 |

OTHER PUBLICATIONS

Sander W., Recycling Auf Hohem Niveau, Plastverarbeiter, Huethig GMBH, Feb. 1, 1995, Bd. 46, Nr. 2, Heidelberg, Germany.
PCT International Preliminary Report on Patentability, PCT/E2017/78813 dated May 21, 2019.
PCT International Search Report, PCT/E2017/78813 dated Mar. 15, 2018.
PCT Written Opinion, PCT/E2017/78813 dated Mar. 15, 2018.

* cited by examiner

*Primary Examiner* — Terressa Boykin
(74) *Attorney, Agent, or Firm* — Morriss O'Bryant Compagni Cannon, PLLC (57) ABSTRACT

The invention relates to a recycling process for contaminated polyolefins, in particular HDPE, wherein the contaminated polyolefin is swelled using a solvent such that contaminants in the polyolefin dissolve in the solvent, and the solvent as well as the contaminants dissolved from the solvent are removed from the polyolefin.

22 Claims, 4 Drawing Sheets

SYSTEM AND PROCESS FOR RECYCLING CONTAMINATED POLYOLEFINS

CROSS-REFERENCE TO RELATED APPLICATIONS

This application is a national phase entry under 35 U.S.C. § 371 of PCT/EP2017/078813 filed Nov. 9, 2017, which claims priority to Swiss Patent Application No. 1523/16 filed Nov. 17, 2016, the entirety of each of which is incorporated by this reference.

TECHNICAL FIELD

The invention, along with a recycling system, relates to a recycling process for contaminated polyolefins, especially HDPE from packaging materials such as drink containers.

PRIOR ART

With resource consumption that increases with population, recycling systems, especially for polymers that are being used, become significant. However, with food packaging, this reuse is severely restricted, because the recycled materials should again be suitable for direct contact with food, which presumes that possible contaminants in the material are not transferred to the food products in impermissible quantities. Ever more strict legal requirements in the area of food products limit the use of recycled material, and therefore result in very poor recycling rates, depending on the type of polymer, especially in the area of packaging. While PET packaging in this regard is relatively unproblematic, and the material from PET bottles (in limited quantities) can again be used for manufacture of PET bottles, there is pent-up demand for polyolefins like HDPE. On the one hand, the multiplicity of HDPE packaging materials makes recycling more difficult and on the other hand, elimination of contaminants from the material of HDPE bottles is a problem that has not yet been satisfactorily solved.

Gradual reduction of an assumed maximum possible contamination (the "challenge test" concentration) to a residual concentration is seen as a measure of decontamination performance of a recycling system, by means of which various recycling processes can be assessed and compared.

Some of the previously evaluated systems are definitely suitable to decontaminate HDPE material, but for this they take so long that commercial utilization is not possible.

Advantages of the Invention

It is an advantage of the present invention to provide an alternative recycling system for contaminated polyolefins, wherein the decontaminated polyolefin material obtained through the system which may be suitable for use in food product packaging. In addition, the method should be able to be carried out economically. Additional advantages of the present invention result from the specification that follows.

Representation of the Invention

The above mentioned advantages are achieved by a method and system for recycling contaminated polyolefins.

What is disclosed, among other things, is a recycling process for contaminated polyolefins, in which a contaminated polyolefin material is swelled in the presence of a solvent, wherein contaminants present in the polyolefin material are dissolved in the solvent, and the solvent and the contaminants dissolved in the solvent are removed from the polyolefin material.

Additionally disclosed is a recycling system for recycling of contaminated polyolefins with a swelling reactor, for example in the form of a stirring vessel or a stirring vessel cascade or a tube reactor, containing a solvent, in which the solvent is a solvent with a lower polarity than water, wherein the swelling reactor is so designed to swell a contaminated polyolefin material in the presence of the solvent, to dissolve contaminants present in the polyolefin material in the solvent. Downstream of the swelling reactor (or as part of the swelling reactor), the recycling system has a system component for removal of the solvent and the contaminants dissolved in the solvent from the polyolefin material, for the purpose of obtaining a decontaminated polyolefin material.

In what follows, features are described, with these (individually) to be considered as desired features, even if they are not designated explicitly as such. The features are to be disclosed separately (as part of any process and/or any system) and in any combination, as long as they do not exclude each other. This includes a possibility of simultaneous implementation of all the described features.

Of especial interest as a polyolefin which can be decontaminated with the aid of the process taught in this document, and/or with the recycling system taught in this document, is HDPE ("high-density polyethylene"). Therefore, in what follows, this polymer is used by example for clarification of the invention. What is disclosed about HDPE can, however, alternatively be disclosed for polyolefins in general and especially for the particular polyolefins named in this document.

Contaminants, especially those from nonpolar (apolar) molecules, can migrate into the HDPE matrix and accumulate there in very high concentrations. They are dissipated from the HDPE matrix at very slow rates, even if very high temperatures (100-300° C.) and a high concentration gradient are used for removal of these contaminants in the recycling process.

With the present invention, the HDPE is to be so altered that it releases contaminants more easily and with less technical effort. For this, the swelling capacity of polyolefins is exploited: a swelled polymer as a rule is more voluminous, with the molecular intervals greater and the density less. Therefore, contaminants are much more quickly diffused outward than in a non-swollen polymer with concentration gradients of contaminants otherwise being the same. In addition, two additional effects can markedly amplify the purification action. On the one hand, a swelled polymer can be squeezed out mechanically like a sponge, which causes many of the contaminants present therein to be removed. On the other hand, upon removal of the solvent used for the swelling, contaminants are carried away.

Therefore, a recycling process for contaminated polyolefins is disclosed, which can be implemented for example in the system described in this document. The recycling process includes the removal of contaminants from a contaminated polyolefin material, especially from areas of the polyolefin material distant from edge surfaces.

Removal of contaminants from the contaminated polyolefin material includes that the contaminated polyolefin material is swollen in the presence of a solvent and/or by a solvent. With this, contaminants present in the polyolefin material can dissolve in the solvent that is present in the polyolefin material. The solvent, and the contaminants dissolved in the solvent, can thereafter be removed together and/or simultaneously from the polyolefin material.

With this, the recycling process can comply with all of the criteria of the European Food Safety Authority (EFSA) in accordance with EU Regulation EC282/2008 and EU Regulation 1935/2004, as well as supplements thereto.

An assessment of the recycling performance of the recycling process can be made by the CEF Panel (EFSA Panel on Food Contact Material, Enzymes, Flavourings and Processing Aids) using a so-called Challenge Test, in which the polyolefin material is contaminated by preset contaminations in preset concentrations, and the concentrations of the contaminations are measured after conducting the recycling process. Through the recycling process, general contaminants can be heavily reduced in their concentrations by benzene, toluene and/or xylene, or even completely eliminated. Through the recycling process, special contaminants like di-term-butylhydroxyltoluene (BHT), phenylcyclohexane, methylstearate, zinc stearate, trichloroethane, butyl salicylate, methylpalmitate, lindane and/or benzophenone can be heavily reduced in their concentration or even completely eliminated. Naturally, also those contaminations can be heavily reduced or even completely eliminated, which are found in the solvent used.

Through the recycling process, decontaminated polyolefin material can be provided which is at least in part suitable for contact with food. Thus, the decontaminated polyolefin material can be used for packaging that is suitable for packaging food products.

The contaminated polyolefin material can be produced from one or more polyolefins, and/or contain a share of polyolefins of altogether at least 60, 80 or 90 percent by weight.

One or more of the polyolefins can advantageously be PP (polypropylene) and/or PE (polyethylene), especially LDPE (low density polyethylene) and/or LLDPE (linear low density polyethylene) and/or HDPE (high density polyethylene) and/or UHMWPE (ultra high molecular weight polyethylene), with HDPE being selected.

Alternatively, or in addition, one or more of the polyolefins can be a thermoplastic elastomer or a plastomer.

The polyolefin material may contain less than 20 or 10 percent by weight of foreign polymers, such as barrier layers.

The contaminated polyolefin material may be present in a solid form, especially when swelled.

Before swelling, the contaminated polyolefin material can be processed into pieces ("flakes", for example) and/or during the swelling it already is in the form of pieces, with the pieces that may be provided with a maximum diameter (distance of the points most distant from each other) of at most 40, 30 or 25 millimeters and/or at least 0.25, 0.5 or 1 millimeter. This facilitates swelling, and, due to the large surface, promotes material exchange and thus decontamination. At least 90 or 95 percent by weight of the contaminated polyolefin material has this shape.

Prior to swelling, the contaminated polyolefin material can be separated from foreign material such as glue or paper, and possibly be sorted by color.

The contaminated polyolefin material advantageously is derived from food product packaging, especially bottles.

According to one variant, the contaminations in the contaminated polyolefin material are so-called NIAS ("non-intentionally added substances").

The contaminants present in the contaminated polyolefin material (especially in the majority and/or in a total share of at least 40, 60, or 80 percent by weight of contaminants) can include molecules which are nonpolar or essentially nonpolar and/or have at least 5, 8 or 10 and/or at most 70, 50 or 40 carbon atoms, and/or a molecular weight of at least 20 Daltons and at most 1000 Daltons.

Alternatively, or additionally, the contaminants present in the contaminated polyolefin material (especially in the majority and/or in an overall share of at least 40, 60 or 80 percent by weight of contaminants) can include materials from one or more of the following material groups: aliphatic saturated hydrocarbons, aliphatic unsaturated hydrocarbons, aliphatic hydrocarbons with functional groups, aromatic hydrocarbons, aromatic hydrocarbons with functional groups, scents (especially terpenes like limes), and flavoring agents.

The contaminants in the contaminated polyolefin material can include molecules (especially in the majority and/or in a total share of at least 40, 60 or 80 percent by weight of contaminants), which fall under the term of MOSH (mineral oil saturated hydrocarbons) and/or under the term of MOAH (mineral oil aromatic hydrocarbons).

By swelling of the contaminated polyolefin material in the presence of the solvent, a swelled polyolefin material is obtained.

The swelling is carried out until the volume of the contaminated polyolefin material has increased by at least 0.3, 0.5 or 0.8, and/or at most 40, 20 or 7 percent, with a volumetric increase by 1 to 5 percent being especially desireable.

The contaminated polyolefin material is swollen at a temperature of at least 0, 100 or 150 degrees Celsius and/or at most about 10° C. below the melting temperature of the respective polyolefin.

Additionally, it is advantageous if the contaminated polyolefin is swelled at an excess pressure, especially at a pressure of at least 1, 50 or 100 bar and/or at most 1000, 500 or 250 bar.

Alternatively or additionally, provision can be made that the contaminated polyolefin material be swelled in the presence of a solvent, with the solvent being in a liquid state or in a supercritical state.

The contaminated polyolefin material can, for example, be swelled for at least 0.5, 1 or 2 hours, and/or at most 10, 5 or 3 hours.

It is advantageous if the polyolefin material and/or the solvent is moved during the swelling, especially relative to each other. For example, the polyolefin material and/or the solvent can be stirred.

According to one variant, the contaminated polyolefin material can be swelled by a percolation process (passage process). With this, the solvent flows past the contaminated polyolefin material, and the contaminated polyolefin material absorbs the solvent. By having the solvent flow past the polyolefin material, it is ensured that solvent laden locally with contaminants flows away, and is replaced by that which is less laden.

According to another variant, the contaminated polyolefin material is swelled by an immersion process. The contaminated polyolefin material is dipped into the solvent, with the polyolefin material and solvent as by being stirred. By this means, an equalization of concentration of contaminants in the solvent is facilitated.

According to another variant, the polyolefin material is swelled while the polyolefin material and the solvent are made to be in counter-flow. At every time of the material exchange, the solvent exhibits a lower concentration of contaminants than the contaminated polyolefin material with which it is in contact, through which the concentration gradient always is dropping from the polyolefin phase in the direction of the solvent phase. For this, contaminated solvent is not fed in, or only in small quantities, where the "leached-out" contaminated polyolefin material is drawn off by suction. Vice versa, there where the contaminated polyolefin material is added, which now is withdrawn with solvent laden with contaminants. This occurs in procedural apparatus, such as tube reactors or stirring vessel cascades, which are known to one skilled in the art.

The solvent, with the contaminants dissolved therein, is designated in this document as "contaminated solvent". The contaminated solvent can be decontaminated and used again as a solvent in the procedure, especially for swelling of contaminated polyolefin material, with the decontamination being able to occur, for example, by means of a distillation or rectification.

The solvent can be a low-polarity solvent, or a nonpolar solvent. On the one hand, the solvent is of lower polarity than water, of equal polarity than acetone, or less. On the other hand, the solvent can have equal or greater polarity than n-hexane.

According to one variant, the solvent can be an alkane, especially n-hexane or n-heptane.

The solvent and the contaminated polyolefin material can have a RED ("relative energy difference") as per Hansen (source Charles M. Hansen: *Hansen Solubility Parameters: a User's Handbook*, $2^{nd}$ edition, CRC Press, Boca Raton 2007, ISBN 0-8493-7248-8) of at most 3, 2 or 1.

The solvent used for this process can consist of a single type of solvent, or of multiple types of solvents, i.e. of a solvent mixture. The solvent may consist of 80, 90 or 95 percent by weight of one type of solvent, so that it is more easily purified.

If the solvent contains more than one type of solvent, then the boiling points of two of the types of solvents used differ by at least 2.5 or 10 degrees Celsius and/or at most by 100, 50 or 30 degrees Celsius, so that they can easily be separated by distillation. Further it is desired if the solvents form no azeotrope.

Removal of the solvent and/or of the contaminants dissolved in the solvent from the polyolefin material can appropriately include mechanical compression of the swelled polyolefin material, through which a pressed-out polyolefin material is obtained. A worm or a bandpass filter press can, for example, be used for mechanical compression of the swelled polyolefin material. By mechanical compression, advantageously at least 60, 80 or 90 percent of the solvent, and/or of the contaminants dissolved in the solvent, can be removed from the polyolefin material.

The swelled polyolefin material may have a volume that is at least 0.3, 0.5 or 0.8 and/or at most 40, 20 or 7 percent greater than the non-swollen polyolefin material and/or than the pressed-out polyolefin material.

According to one variant, the procedural step in which the polyolefin material is swelled, and the procedural step in which the swollen polyolefin material is subjected to a mechanical compression, can each be conducted one time. Alternatively, the named procedural steps can be carried out multiple times (for example, twice, thrice or more times) during the process, and/or with the same polyolefin material.

For example, provision can be made that the swelled polyolefin material be subjected to mechanical compression, with one part (especially at least 30, 20 or 10 percent) of the (contaminated) solvent present in the swelled polyolefin material being removed from the polyolefin material. Then the pressed-out polyolefin material obtained can be swelled again in the presence of one (i.e., the same or another, or a decontaminated) solvent, with the (residual) contaminants present in the polyolefin material dissolving in the solvent. Thereafter the swollen polyolefin material obtained is again subjected to mechanical compression. According to one variant, the solvent, after one, or each, mechanical compression, can be decontaminated, before it is again used for swelling. According to another variant, this decontamination can be dispensed with.

The recycling process and/or the removal of the solvent (with contaminants dissolved in the solvent) from the polyolefin material can include an (initial) drying of the polyolefin material (especially of the pressed out polyolefin material) in a drier, with solvent remaining in the polyolefin material being vaporized, through which a dried polyolefin material is obtained.

Although this does not have to be the first drying of the polyolefin material, this drying is designated as the "(initial) drying", (merely) to distinguish it from the "second drying", described below.

Advantageously the polyolefin material is impinged on for the (initial) drying by a gas, especially an inert gas such as nitrogen. The vaporized solvent can for example be recovered by a refrigeration gradient from the gas.

It is also conceivable that the (initial) drying be carried out in a vacuum and/or in a vacuum drier, and/or that it is carried out at reduced pressure, especially at an absolute pressure below 1 (medium vacuum), 300 (low vacuum), or 1013 (reduced pressure) mbar.

The (initial) drying may be carried out at a temperature that (at least 5 or 10 degrees Celsius and/or at most 50, 30 or 20 degrees Celsius) is below the melting temperature (peak temperature as per ISO11357-3-2013) of the polyolefin material, and/or the gas, by which the polyolefin material is impinged on for the (initial) drying, has such a temperature.

In sensible fashion, the (initial) drying is carried out at a temperature that is above the boiling temperature of the solvent and/or of the contaminants remaining in the polyolefin material.

The (initial) drying is carried out at a pressure of at least 1, 300 or 1013 mbar absolute, and/or at most the vapor pressure of the solvent at the corresponding drying temperature.

The (initial) drying is carried out for a duration of at least 60, 30 or 10 minutes, and/or at most 30, 20 or 10 hours.

The drier used for the (initial) drying of the polyolefin material, can, for example, be a drum drier or a fluidized bed drier.

The recycling process and/or the removal of contaminants from the contaminated polyolefin material can include a melting and extruding of the polyolefin material (especially of the dried polyolefin material). Then the polyolefin can be granulated, through which a polyolefin granulate is obtained.

For the extrusion, an extruder with a degasification zone may be used. By this means, the solvent remaining in the polyolefin material can be removed.

Additionally, provision can be made that the polyolefin material is subjected to a melt filtration.

Upon removal of the solvent and/or of the contaminants from the polymer material, also usable additives can be removed from the polymer material. Therefore, provision can be made that one or more additives (especially in essence the same additives which previously were removed) are added to the polyolefin material in a molten state. The one or more additives can, for example, be one or more process stabilizers such as antioxidants.

The recycling process and/or the removal of contaminants from the contaminated polyolefin material can include a (second) drying, especially a vacuum drying, of the polyolefin material (especially of the polyolefin granulate). The drying can, for example, be carried out in a solid state polycondensation or SSP reactor.

Although this does not have to be the second drying of the polyolefin material, this drying is designated as the "(second) drying", (merely) to distinguish it from the "initial drying" described above.

The (second) drying may be carried out at reduced pressure (especially at a pressure below 1013 mbar (atmospheric pressure under normal conditions)) and/or in a vacuum under 50 mbar. Alternatively, the (second) drying can be carried out at excess pressure, especially at a pressure up to the vapor pressure of the particular solvent at the corresponding drying temperature, and/or the polyolefin material can be impinged on for drying by a gas, especially an inert gas such as nitrogen.

The (second) drying is appropriately carried out at a temperature which (at least 5 or 10 degrees Celsius and/or at most 50, 30 or 20 degrees Celsius) is below the melting temperature (peak temperature as per ISO11357-3-2013) of the polyolefin material, and/or the gas, by which the polyolefin material optionally is impinged on for drying, has such a temperature.

The (second) drying is carried out at a pressure of at least 1 mbar, 5 mbar or 50 mbar, and/or at most 1 bar, 10 bar or 100 bar.

The (second) drying is carried out for a duration of at least 1 minute, 5 minutes or 10 minutes, and/or at most 30 hours, 20 hours or 10 hours.

Additionally, the drying can occur in an atmosphere that consists of nitrogen of at least 99, 98, 98 or 90 percent by volume.

Additionally disclosed is a recycling system for the recycling of contaminated polyolefins, especially for conducting the recycling process disclosed in this document, and/or for removal of contaminants from a contaminated polyolefin material. The polyolefin material especially may be the polyolefin material described above in connection with the recycling process.

According to one variant, the recycling system can be an upgraded or converted PET recycling system, i.e., a system for recycling of polyethylene terephthalate.

The recycling system has a swelling reactor, for example in the form of a stirring vessel or a cascade of stirring vessels or a tube reactor. The swelling reactor contains a solvent, with the solvent being a solvent with a polarity less than water and/or a solvent described in connection with the recycling process. The swelling reactor is so configured to swell contaminated polyolefin material in the presence of the solvent, to dissolve or rinse out contaminants present in the polyolefin material in the solvent.

The swelling reactor can be configured to swell the contaminated polyolefin material at the temperature/and or pressure and/or during the time described further above in connection with the process, in the presence of the solvent. Especially the swelling reactor can be configured to swell the contaminated polyolefin material at a temperature of about 10° C. below the melting temperature of the particular polyolefin material and/or at a pressure between 1 and 1000 bar in the presence of the solvent.

Additionally, the swelling reactor is configured so that it moves the polyolefin material during the swelling, especially by stirring. For this purpose, the swelling reactor has a stirrer device, for example.

Provision can be made that the swelling reactor be configured to swell the polyolefin material by means of a percolation process, an immersion process, or have the polyolefin material and the solvent brought together in a counter-flow, especially as this was described above in connection with the recycling process.

The recycling system has a system component placed downstream of the swelling reactor (that is, arranged downstream thereof), for removing the solvent and the contaminants dissolved in the solvent, from the polyolefin material.

Especially such a system component can have a filter to filter out the solvent and/or means for pressing out the swelled polyolefin material.

Appropriately, the recycling system has one or more separation stages and/or wash stages placed upstream of the swelling reactor (that is, arranged upstream thereof).

These can be configured for separating out foreign materials, for example paper labels, from the polyolefin material.

Advantageously the recycling system can have one or more of the following separation stages, especially placed upstream of the swelling reactor in the sequence given: a metal remover, for removing magnetic and/or non-magnetic metals; a label remover, for removal of labels; a ballistic sorter, for removal of foils; a bottle sorter, for sorting by color; a manual sorting stage; an air separator (for example, for removal of labels and sleeves); a float-sink-stage, for separation by lowering in water; a sorting stage by means of NIR (near infrared spectroscopy) for separating out foreign plastics and/or dust.

The recycling system can advantageously have one or more of the following wash stages, (especially, placed upstream of the swelling reactor in the sequence indicated): a wash stage with water and if necessary one or more detergent substances such as a lye, for example; a hot-water wash stage, for example for removal of paper and cardstock; a wash stage for subsequent washing with water and/or for neutralizing the lye.

After separating and/or washing, the polymer material can be dried, before it is brought to the swelling reactor. Thus, a drier may be placed between the separating and/or washing stages placed upstream of the swelling reactor, and the swelling reactor.

The recycling system can have a mill for comminution of the products manufactured from polyolefin material, such as containers and caps. The fragment sizes are indicated above in connection with the method, with particular preference for processing into flakes.

The mill can, for example, be placed downstream from one or more of the above-mentioned separating stages and/or upstream of one or more of the above-mentioned wash stages. In particular, the polymer material can be washed after the comminution.

Additionally, the recycling system can have a drier placed downstream of the swelling reactor, as is described for example above in connection with the (initial) drying.

A system component placed downstream of the swelling reactor for cleaning the solvent, especially by means of distillation or rectification, and for recycling the purified solvent into the swelling reactor, is likewise also provided.

Lastly, a purified polyolefin material is to be disclosed, manufactured by a process described in this document and/or by means of a recycling system described in this document, with the purified polyolefin material present in the form of a granulate.

The terms in this document are to be understood as they would be understood by one skilled in the art in this field. If multiple interpretations are possible in the given context, then each interpretation is individually disclosed. Especially in cases where there may be items lacking in clarity, alternatively, or supplementally, the definitions presented in this document are applied.

If mention is made in this document of removal of contaminants from the polyolefin dissolved in the solvent, then alternatively a removal of contaminants present in the polyolefin is disclosed. This is because the decontamination steps such as SSP not only are capable of removing dissolved contaminants from the polyolefin, but also such that are not dissolved in the polyolefin.

Additionally, the following patent claims are each disclosed with a reference back to any of the foregoing claims ("of one of the foregoing claims"), even if they are not claimed in this form.

BRIEF DESCRIPTION OF THE DRAWINGS

Shown are.

IMPLEMENTATION OF THE INVENTION

The invention is described in the following in an exemplary manner by means of the figures.

FIGS. 1a to 1d depict the sequence of a recycling process. The process in essence consists of 4 parts:

In a first part (shown in FIG. 1a), the polyolefin is sorted and then comminuted.

In a second part (shown in FIG. 1b), the comminuted polyolefin material is washed, dried and if necessary sorted once more.

In a third part (shown in FIG. 1c), contaminants from the washed and dried polyolefin material are removed, in that it is swollen by means of a solvent, with the contaminants present in the polyolefin material being dissolved in the solvent. Then the solvent and the contaminants dissolved therein are separated from the polyolefin material, first mechanically, and then the solvent residues are removed in a drier.

In a fourth part (shown in FIG. 1d), the polyolefin material, after passing through an optional additional step, is extruded in molten form, granulated, and fed to an SSP reactor, where it is subjected to a vacuum treatment.

Figure 1A:
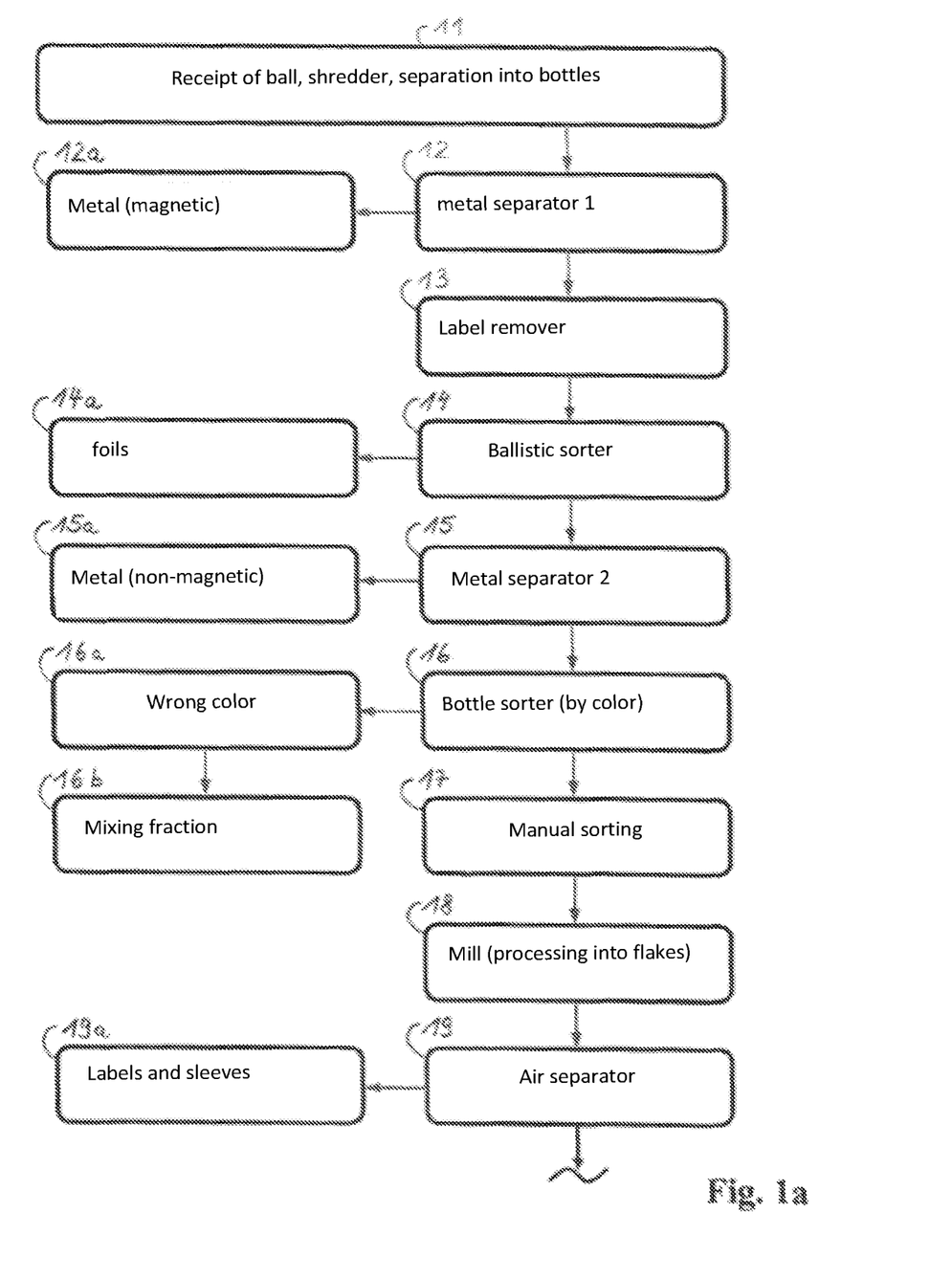
FIGS. 1a-d show a recycling system (flow chart in 4 parts, in the sequence 1a, 1b, 1c, 1d)

FIG. 1a: the polyolefin material to be cleaned is derived, for example, from containers, especially bottles and caps, and can be delivered in the form of bales to the recycling facility. The bales are taken apart in the recycling facility (11). The containers are fed to a first metal separator (12), which separates out magnetic metal (12a). Then the containers pass through a separator stage for removal of labels, i.e., a "label remover" (13), before they are fed to a ballistic sorter (14), which removed the foils (14a). In a second metal separator (15), non-magnetic materials (15a) are separated out, with a sorting taking place thereafter by colors in a (colored) bottle sorter (16), which sorts out containers with other than the desired color (16a) and collects them in a mixing fraction (16b). Then the sorted containers are chopped in a mill (18) into flakes, which are separated from their labels and sleeves (19a) in an air separator (19).

Figure 1B:
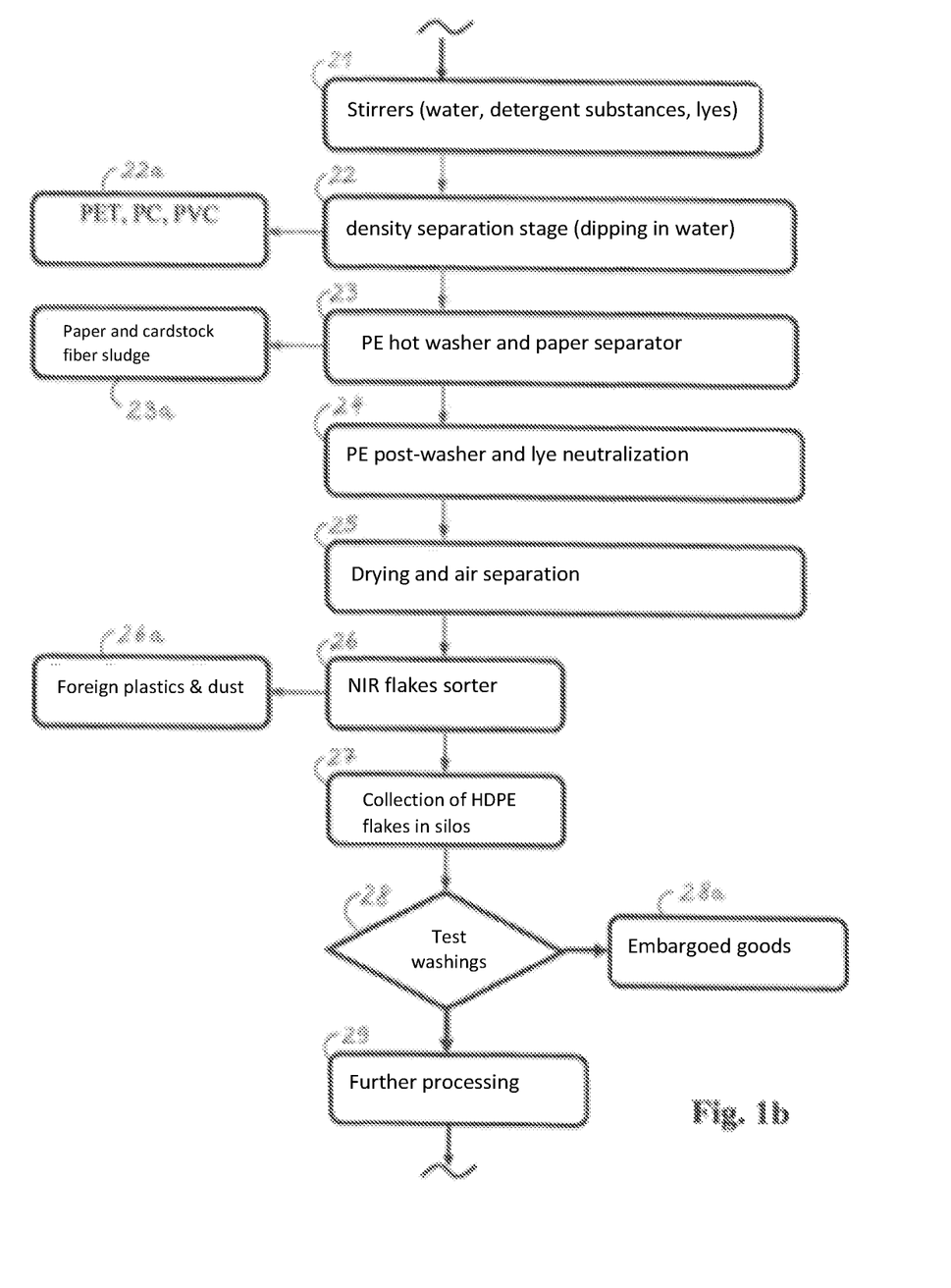

FIG. 1b: the flakes are washed with water and detergent substances such as a lye (21), separated by density in a separation stage (22), with foreign polymers such as PET, PC and/or PVC (22a) being sorted out. A subsequent wash in hot water (23) serves for removal of paper and cardstock fibers (23a), which is present in the form of a sludge. A subsequent wash, if a lye was previously used, can also serve for lye neutralization (24), with the flakes, after passing through the wash stages, being dried, and fed to an air separator (25). By means of an NIR spectrometer (26), residual foreign plastics (26a) can be identified, was makes possible a sorting out of same. The flakes lastly are drawn off (27) and tested (28). If they fail to pass the test, they flakes are sorted out as embargoed goods (28a). If the flakes pass the test, they undergo further processing (29).

Figure 1C:
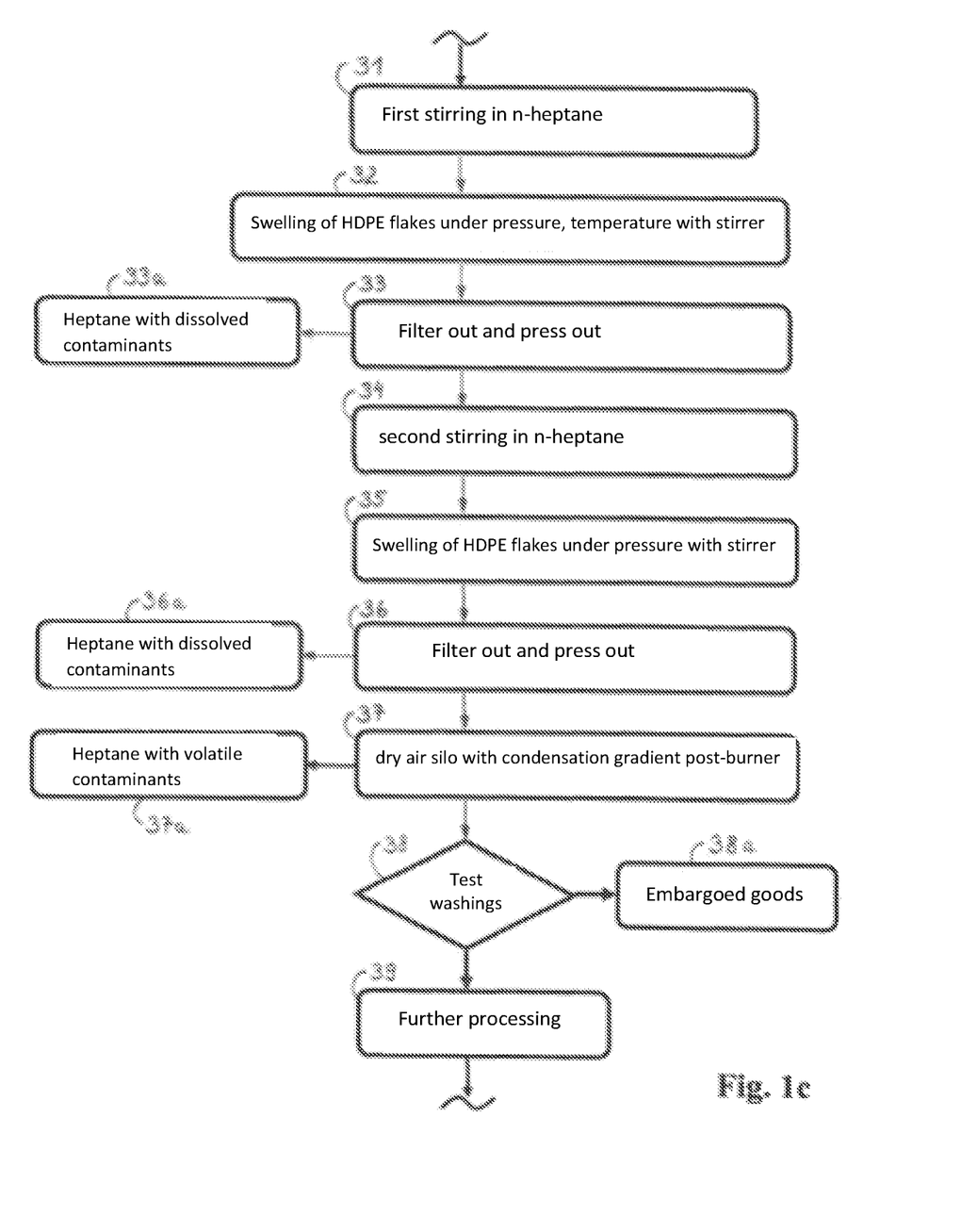

FIG. 1c: A solvent, in the present case n-heptane, is added to the flakes, and the flakes are initially mixed with the solvent by stirring (31). At increased pressure and increased temperature, the flakes absorb the solvent, i.e., they swell (32). Solvent not absorbed by the flakes is removed through a filter and the flakes then are pressed out (33), through which solvent present in the flakes, and contaminants (33a) dissolved therein, are removed from the flakes. The above-mentioned steps are repeated one or more times (34, 35, 36) to remove remaining contaminants (36a) in the flakes. The pressed out flakes lastly are dried (37), with solvent remaining in and on the flakes together with the remaining volatile contaminants (37a) being vaporized. The solvent and the contaminants can be separated by means of a refrigeration gradient, with the contaminants being able to be subject to combustion in a burner (37). The dried flakes are then tested again (38). Only those flakes that pass the test are subject to further processing (33), with the rest being sorted out as embargoed goods (38a).

Figure 1D:
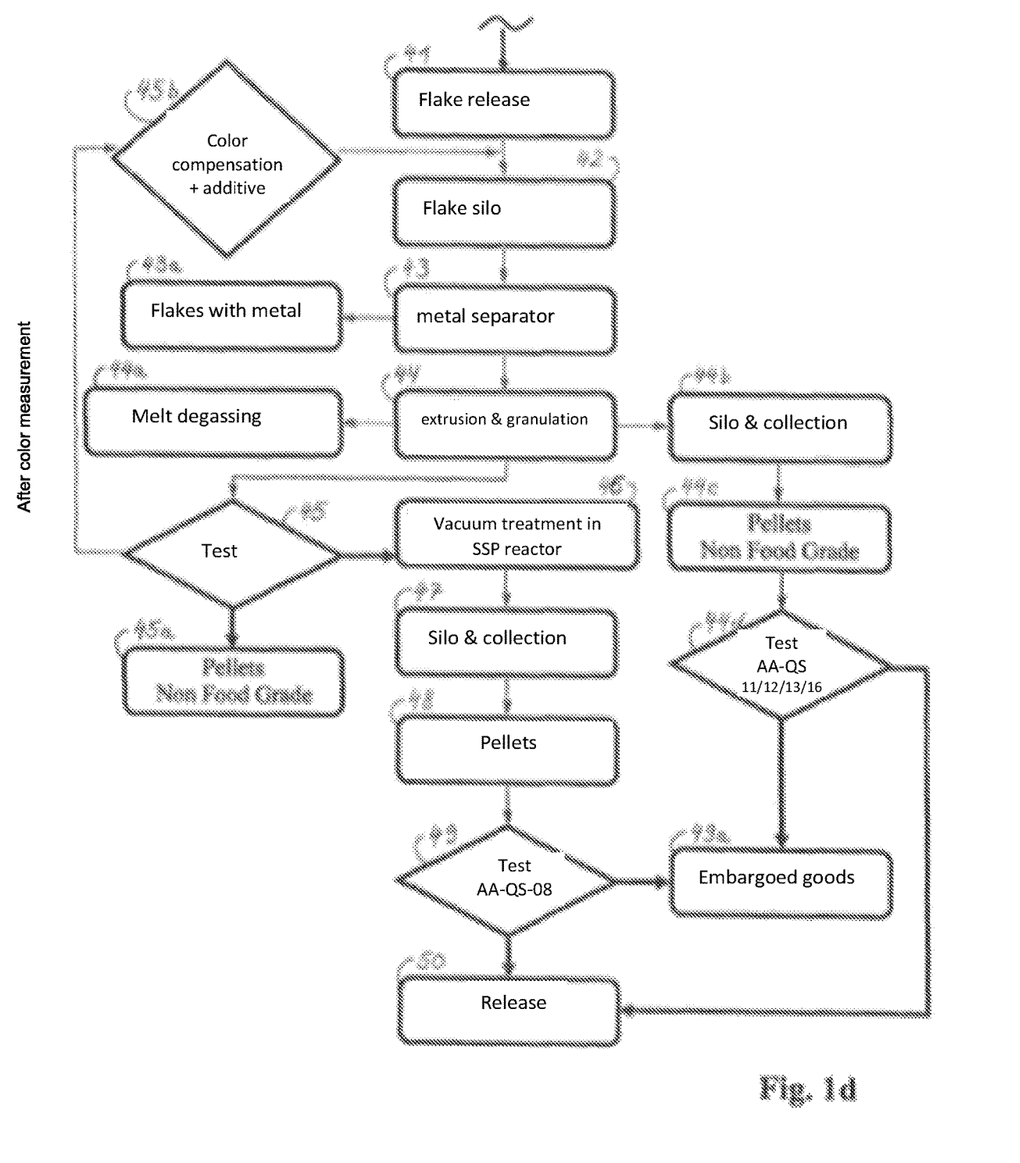

FIG. 1d: The flakes (41) which were collected in a silo (42) are brought optionally to a (third) metal separator (43) in which the flakes are removed from the metal (43a). Additionally, the flakes are melted, extruded and granulated (44), with the extrusion able to include a melt-degassing (44a), through which residual solvent and/or volatile contaminants can be removed.

The polyolefin granulate (44c) generated by the granulation can be collected and drawn off (44b). This granulate (44c), possibly not yet suitable for use in the food products industry, can be tested (44d). If it passes the test it is released for use for food product packaging (50), and if it fails to pass the test, it is sorted out (embargoed goods, 49a).

Alternatively, after granulation the polyolefin material can be tested (45). If the granulate color does not conform to the requirements, additives (45b) can be fed in, with the polyolefin material thus modified able to be recycled back into the silo (42). If the granulate passes the test (45), it can be made available for applications outside the food industry (45a), or it is fed to an SSP reactor (46) in which it is subject to a vacuum treatment. The granulate thus treated is collected (47) and is provided (48) for use in the food products industry, where, prior to release (50) for this purpose, it is tested (49). If it passes the test, it is released (50), and if it fails to pass the test, it is sorted out as embargoed goods (49a).

The invention claimed is:

1. A method of recycling contaminated polyolefins, including removal of contaminants from a contaminated polyolefin material, comprising:
    swelling a contaminated polyolefin material with a solvent causing contaminants in the polyolefin material to dissolve in the solvent; and
    removing the solvent and the contaminants in the solvent from the polyolefin material, whereby removing the contaminants dissolved in the solvent from the polyolefin material includes a compression of the swollen polyolefin material, through which a majority of the solvent is pressed out of the swollen polyolefin material.

2. The method of claim 1, wherein the polyolefin material consists essentially of polyethylene or polypropylene.

3. The method of claim 1, further comprising drying the polyolefin in a drier after pressing the swollen polyolefin to vaporize solvent remaining in the polyolefin material.

4. The method of one of claim 1, further comprising melting and extruding the polyolefin material to remove residual solvent from the polyolefin material, the polyolefin material then being granulated to form a polyolefin granulate.

5. The method of claim 4, further comprising using an extruder having a degasification zone to extrude the polyolefin.

6. The method of claim 4, further comprising heating the polyolefin granulate in a solid-state condensation reactor or in a vacuum.

7. The method of one claim 1, further comprising comminuting the contaminated polyolefin material to flakes and foreign material and separating the foreign materials from the contaminated polyolefin material by one or more sorting methods comprising a dry sorting method or at least one washing step in water.

8. The method of claim 1, wherein the swelling the contaminated polyolefin material is at a temperature of about 10° C. below a melting temperature of the polyolefin material, and at a pressure between 1 and 1000 bar, for at least 5 minutes, and moving the polyolefin in the solvent during the swelling.

9. The method of claim 1, wherein the swelling the contaminated polyolefin material causes a volume of the contaminated polyolefin material to increase through the swelling by at least 1 percent.

10. The method of claim 1, wherein the solvent has a lower polarity than water.

11. The method of claim 1, wherein the solvent is an alkane comprising n-hexane or n-heptane.

12. A recycling system for recycling contaminated polyolefins, comprising:
 a swelling reactor containing a solvent, the solvent having a lower polarity than water, with the swelling reactor configured to swell a contaminated polyolefin material in the presence of the solvent and to dissolve contaminants present in the polyolefin material in the solvent; and
 a system component comprising a system to compress swollen polyolefin material placed downstream of the swelling reactor to remove the solvent and the contaminants dissolved in the solvent from the polyolefin material and to compress the swollen polyolefin material.

13. The recycling system of claim 12, wherein the recycling system comprises an upgraded or converted PET recycling system.

14. The recycling system of claim 12, further comprising separation and washing stages placed upstream of the swelling reactor for separating out foreign materials from the polyolefin material and a drier placed downstream of the swelling reactor.

15. The recycling system of claim 12, wherein the system component placed downstream of the swelling reactor to remove the solvent from the polyolefin material further comprises a drier.

16. The recycling system of claim 12, wherein the swelling reactor comprises a stirring vessel, a stirring vessel cascade or a tube reactor.

17. The recycling system of claim 12, further comprising a granulator downstream of the swelling reactor for melting, extruding and granulating the polyolefin material.

18. The recycling system of claim 12, further comprising a purification system downstream of the swelling reactor to purify the solvent.

19. The recycling system of claim 18, wherein the purification system comprises a means of distillation or rectification and a means to recycle the purified solvent back into the swelling reactor.

20. The recycling system of claim 12, wherein the swelling reactor is configured to swell the contaminated polyolefin material with the solvent at at least one of a temperature of about 10° C. below a melting temperature of particular polyolefin material or a pressure between 1 and 1000 bar.

21. A purified polyolefin material manufactured by a method of recycling contaminated polyolefins, including removal of contaminants from a contaminated polyolefin material, the method comprising:
 swelling a contaminated polyolefin material with a solvent causing contaminants in the polyolefin material to dissolve in the solvent; and
 removing the solvent and the contaminants in the solvent from the polyolefin material to produce the purified polyolefin material, whereby removing the contaminants in the solvent from the polyolefin material includes compressing the swollen polyolefin material, through which a majority of the solvent is pressed out of the swollen polyolefin material.

22. The purified polyolefin material of claim 21, wherein the purified polyolefin material is manufactured by a method of recycling contaminated polyolefin using a recycling system for recycling contaminated polyolefins, the recycling system comprising:
 a swelling reactor containing a solvent, the solvent having a lower polarity than water, with the swelling reactor configured to swell a contaminated polyolefin material in the presence of the solvent and to dissolve contaminants present in the polyolefin material in the solvent; and
 a system component comprising a system to compress swollen polyolefin material to compress the swollen polyolefin material placed downstream of the swelling reactor to remove the solvent and the contaminants dissolved in the solvent from the polyolefin material producing the purified polyolefin material.

* * * * *